US011654210B2

(12) United States Patent
Sivagaminathan et al.

(10) Patent No.: US 11,654,210 B2
(45) Date of Patent: May 23, 2023

(54) INTERACTIVE AROMA DISPENSING SYSTEM

(71) Applicant: Givaudan SA, Vernier (CH)

(72) Inventors: Rahul Karthik Sivagaminathan, Blue Ash, OH (US); Yong Hua Xu, Mason, OH (US); Joseph Kaiser, Alexandria, KY (US)

(73) Assignee: Givaudan SA, Vernier (CH)

( * ) Notice: Subject to any disclaimer, the term of this patent is extended or adjusted under 35 U.S.C. 154(b) by 71 days.

(21) Appl. No.: 17/050,536

(22) PCT Filed: Apr. 29, 2019

(86) PCT No.: PCT/EP2019/060947
§ 371 (c)(1),
(2) Date: Oct. 26, 2020

(87) PCT Pub. No.: WO2019/211243
PCT Pub. Date: Nov. 7, 2019

(65) Prior Publication Data
US 2021/0187148 A1    Jun. 24, 2021

Related U.S. Application Data

(60) Provisional application No. 62/667,055, filed on May 4, 2018.

(51) Int. Cl.
*G06Q 30/0601*    (2023.01)
*A61L 9/12*    (2006.01)
(Continued)

(52) U.S. Cl.
CPC ............ *A61L 9/125* (2013.01); *G06F 3/0482* (2013.01); *G06F 3/0488* (2013.01);
(Continued)

(58) Field of Classification Search
CPC ...... G06F 3/0482; G06F 3/0488; G06F 3/041; G06Q 30/0621; G06Q 30/0631;
(Continued)

(56) References Cited

U.S. PATENT DOCUMENTS 11,410,218 B1 * 8/2022 O'Brien ............. G06Q 30/0633
2003/0014324 A1 * 1/2003 Donovan ........... G06Q 30/0617
705/26.5

(Continued)

FOREIGN PATENT DOCUMENTS

| GB | 2462274 A | 2/2010 |
|---|---|---|
| WO | 0107094 A1 | 2/2001 |
| WO | 2016011372 A2 | 1/2016 |

OTHER PUBLICATIONS

Great Britain Search Report for Application No. 1812451.1 dated Feb. 1, 2019.

(Continued)

*Primary Examiner* — Dino Kujundzic
(74) *Attorney, Agent, or Firm* — Curatolo Sidoti & Trillis Co., LPA; Salvatore A. Sidoti

(57) ABSTRACT

An aroma dispensing system is provided. The aroma dispensing system includes an aroma blending device adapted to deliver at least one aroma substance to the nasal cavities of a consumer; a user interface configured for inputting and displaying information regarding the at least one aroma substance, and a memory component that stores a computer algorithm, the computer algorithm causing the system to analyze the input information in real-time in order to classify aroma preferences of the consumer, including recommending one or more in-store consumer products suitable to the consumer's aroma preferences.

12 Claims, 9 Drawing Sheets

(51) Int. Cl.
  *G06F 3/0482* (2013.01)
  *G06F 3/0488* (2022.01)
(52) U.S. Cl.
  CPC ..... *G06Q 30/0621* (2013.01); *G06Q 30/0631* (2013.01); *G06Q 30/0643* (2013.01)
(58) Field of Classification Search
  CPC ........... G06Q 30/0643; G06Q 30/0268; G06Q 30/0629; G07G 1/12; G07G 17/18; A61L 9/125; A61L 2209/111
  See application file for complete search history.

(56) References Cited

U.S. PATENT DOCUMENTS

| | | | |
|---|---|---|---|
| 2004/0107053 | A1 | 6/2004 | Pelletier |
| 2007/0148293 | A1* | 6/2007 | Lindsay .................... B65D 5/42 426/112 |
| 2008/0131858 | A1* | 6/2008 | Gordon .............. G09B 19/0076 434/327 |
| 2012/0018528 | A1 | 1/2012 | Samain |
| 2012/0085829 | A1* | 4/2012 | Ziegler ..................... G09F 3/14 235/487 |
| 2012/0247613 | A1 | 10/2012 | Behbehani |
| 2013/0117137 | A1* | 5/2013 | Klein ...................... G07F 17/26 705/16 |
| 2013/0120771 | A1* | 5/2013 | Wang ................. H04N 1/32133 358/1.9 |
| 2013/0189405 | A1* | 7/2013 | Filliol ................... A47J 31/525 99/287 |
| 2015/0048178 | A1* | 2/2015 | Edwards ............ H04N 21/4112 239/128 |
| 2016/0363917 | A1* | 12/2016 | Blackley ............... G06F 3/0488 |
| 2017/0018000 | A1* | 1/2017 | Cameron ........... G06Q 30/0269 |
| 2017/0091853 | A1* | 3/2017 | Cameron ........... G06Q 30/0637 |
| 2017/0169436 | A1* | 6/2017 | Ur .......................... A61L 9/015 |
| 2017/0266676 | A1* | 9/2017 | Fateh ................... A63F 13/212 |
| 2018/0373272 | A1* | 12/2018 | Kihm ................... B05B 12/004 |
| 2019/0370878 | A1* | 12/2019 | Tran .................. G06Q 30/0631 |
| 2020/0078485 | A1* | 3/2020 | Suarez Iribarne ...... A61L 9/125 |
| 2020/0084411 | A1* | 3/2020 | Kim ...................... A61L 9/125 |
| 2020/0218415 | A1* | 7/2020 | Jang ........................ G06N 20/00 |
| 2021/0397758 | A1* | 12/2021 | Haeni ............... G06Q 30/0621 |

OTHER PUBLICATIONS

International Search Report for Application No. PCT/EP2019/060947 dated Jul. 16, 2019.
International Written Opinion for Application No. PCT/EP2019/060947 dated Jul. 16, 2019.

* cited by examiner

INTERACTIVE AROMA DISPENSING SYSTEM

CROSS REFERENCE TO RELATED APPLICATIONS

This application is a national stage application of International Application No. PCT/EP2019/060947, filed 29 Apr. 2019, which claims priority from U.S. Provisional Patent Application No. 62/667,055, filed 4 May 2018, both of which applications are incorporated herein by reference in their entireties.

FIELD OF THE INVENTION

The present disclosure relates to an interactive aroma dispensing system. More particularly, the present disclosure relates to techniques, methods, systems and mechanisms for a visual interface between a consumer and an aroma blending device for enhanced user experience and driver of consumer insights. Another aspect of the present disclosure relates to a method that enables consumers to experience the aromas of products prior to making in-store purchasing decisions.

BACKGROUND OF THE INVENTION

At present, online/e-commerce marketing channels remain inferior to in store channels for many items that are targeted to a sense of touch, taste, vision or smell. A consumer may purchase a food or beverage using an online supplier, if that product is a food or beverage which the consumer is intimately familiar with and often purchases. It is unlikely, however, that a consumer will purchase a presently unknown food or beverage from the online supplier, since the purchase would be made relatively blindly. Instead, a consumer would more likely be interested in a new food or beverage after being exposed to it within a retail/grocery store, assuming the aroma is pleasant to the consumer.

As an example, a new food or beverage product may be available on a store shelf, packaged such that a consumer may not have the ability to smell or taste the product, apart from viewing the packaging. While the packaging may include pictures, icons and/or descriptions regarding its taste and aroma, consumers often are still left with uncertainty regarding whether the product would be enjoyable. In earlier eras, consumers may have been able to enter marketplaces or bakeries and directly experience food or beverage samples with all five of their senses. Aside from limited and very costly (to the advertiser) free sample kiosks in some stores, and the fruits/vegetables counters, it is rarely possible for modern consumers to experience many food products with more than their visual senses prior to purchase.

Similar problems exist for products with important attributes dependent upon tactile aspects (i.e., relating to a sense of touch) and/or to products like perfume (i.e., relating to a sense of smell). No known conventional system combines an e-retailing visual and/or audio interface of an automated system with sensory output mechanisms for aroma and/or tastes to permit potential consumers to experience these aspects of a purchasable item. As such, methods are needed that enable consumers to make better informed product selections prior to purchase.

SUMMARY OF THE INVENTION

In one embodiment, an interactive aroma dispensing system is provided. The system includes an aroma blending device adapted to deliver at least one aroma substance to the nasal cavities of a consumer; a user interface configured for inputting and displaying information regarding the at least one aroma substance; and a memory component that stores a computer algorithm, the computer algorithm causing the system to analyze the input information in real-time in order to classify aroma preferences of the consumer, including recommending one or more in-store consumer products suitable to the consumer's aroma preferences.

In another embodiment, a method for sampling an aroma associated with an in-store consumer product is provided. The method comprises the steps of: (a) receiving identifying information from at least one consumer product; (b) identifying the consumer product; (c) retrieving data for the consumer product; (d) displaying an image of the consumer product along with at least one menu option; (e) selecting the menu option to sample the aroma associated with the consumer product; (f) generating at least one aroma substance for the selected consumer product; and (g) delivering the generated aroma substance to the nasal cavities of a consumer.

In another embodiment, a method for recommending an in-store consumer product matching a consumer's aroma profile is provided. The method comprises the steps of: (a) displaying a screen having a plurality of selectable menu options related to aromas; (b) selecting the menu option associated with a particular aroma; (c) generating a set of aroma substances one by one for evaluation; (d) delivering the set of generated aroma substance to the nasal cavities of a consumer one by one; (e) collecting input information from a consumer regarding liking or disliking for each generated aroma substance; (f) analyzing the input information in order to classify the aroma preferences of the consumer in real-time; (g) using the analysis from step (f) to generate a customized aroma profile for the consumer; and (h) recommending one or more in-store consumer products matching to the consumer's aroma profile.

These and other features, aspects and advantages of specific embodiments will become evident to those skilled in the art from a reading of the present disclosure.

BRIEF DESCRIPTION OF THE DRAWINGS

The embodiments set forth in the drawings are illustrative in nature and not intended to limit the invention defined by the claims. The following detailed description of the illustrative embodiments can be understood when read in conjunction with the following drawings, where like structure is indicated with like reference numerals and in which:

Figure 1:
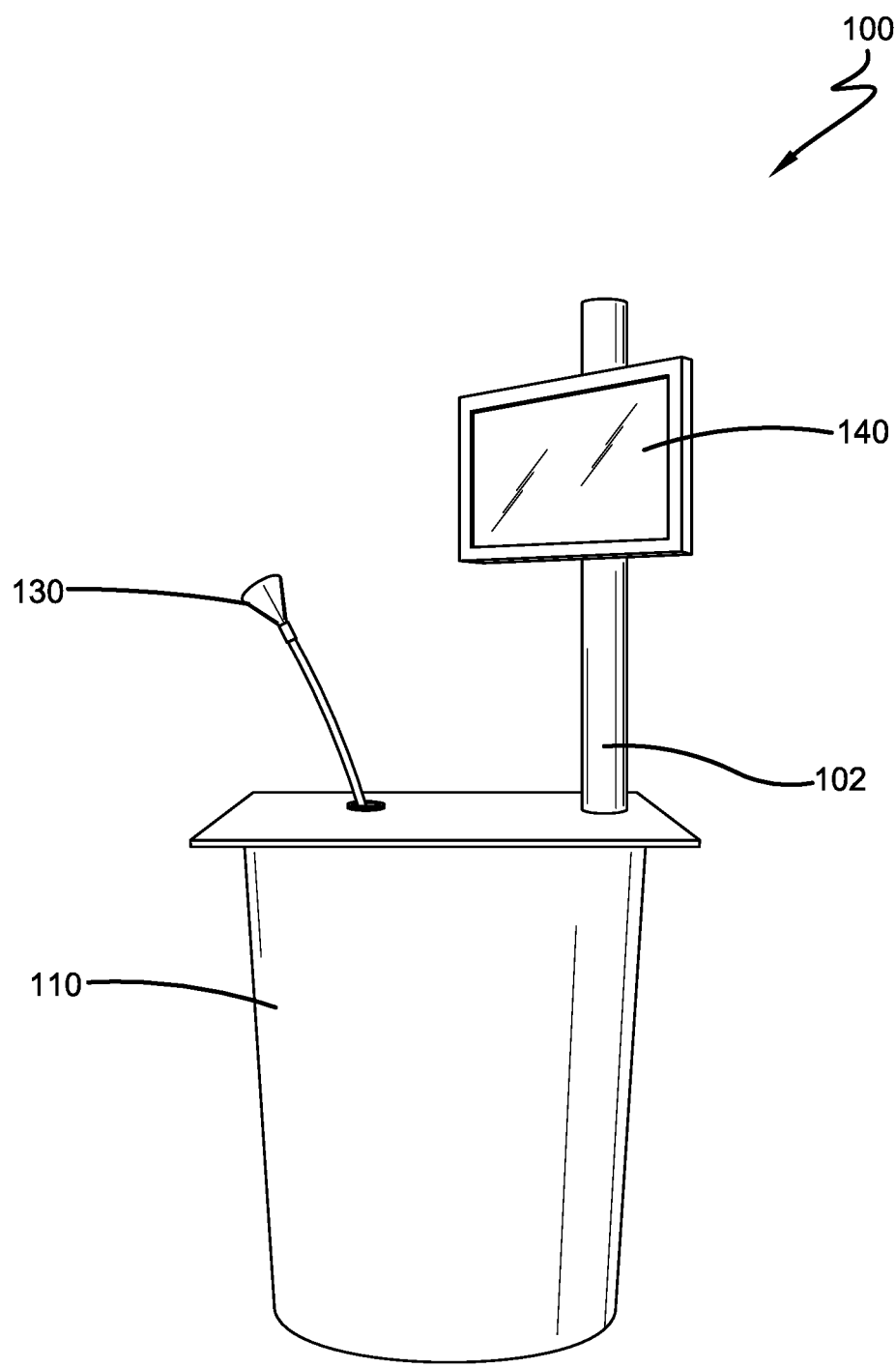
FIG. 1 depicts an interactive aroma dispensing system according to embodiments shown and described herein.

The embodiments set forth in the drawings are illustrative in nature and not intended to be limiting of the disclosure defined by the claims. Moreover, individual features of the drawings and disclosure will be more fully apparent and understood in view of the detailed description.

DETAILED DESCRIPTION OF THE INVENTION

The following text sets forth a broad description of numerous different embodiments of the present disclosure. The description is to be construed as exemplary only and does not describe every possible embodiment since describing every possible embodiment would be impractical, if not impossible. It will be understood that any feature, characteristic, component, composition, ingredient, product, step or methodology described herein can be deleted, combined with or substituted for, in whole or part, any other feature, characteristic, component, composition, ingredient, product, step or methodology described herein. Numerous alternative embodiments could be implemented, using either current technology or technology developed after the filing date of this patent, which would still fall within the scope of the claims. All publications and patents cited herein are incorporated herein by reference.

The present disclosure describes various embodiments of an interactive aroma dispensing system for sampling aroma substances and associated methods. Interactive aroma dispensing systems can be configured to provide information and/or dispense aroma substances without the presence of a salesperson or vendor. In one embodiment, a system may dispense aroma substances characteristic of an in-store consumer product so that consumers can experience the products with more than their visual senses prior to purchase. In another embodiment, the system may be configured to provide consumers with coupons for a discount on a product that the consumer indicated that they liked based on the aroma substance that they sampled. In other embodiments, companies may use or rent an interactive aroma dispensing system in order to promote a particular consumer product or products in exchange for consumer information that is collected, for example, product preference information. In another embodiment, the interactive aroma dispensing system may be configured to provide consumers the ability to "build a flavor" based on a series of questions, sampling aromas and input received from the consumer, for example aroma profiles related to mango, i.e. do you like green or ripe mango. In another embodiment, the interactive aroma dispensing system may be configured to collect information from consumers related to personality or feelings of the consumer and based on the consumer's responses, the system may recommend particular foods or fragrances or products to purchase. Various embodiments of systems are described herein with exemplary references to food and beverage products. Although, the embodiments described herein in detail are directed towards consumables, for example food and beverages, the disclosure is applicable to fragrances and various fragrance containing cosmetic and personal care products, such as for example, candles, fabric and air freshening sprays and body deodorants, laundry detergents and additives, room fresheners or room deodorants, household cleansers, toilet bowl cleaners, dish detergents, body washes, shampoos, conditioners and the like.

According to the present disclosure, the term "consumable" refers to products for consumption by a subject, typically via the oral cavity (although consumption may occur via non-oral means such as inhalation), for at least one of the purposes of enjoyment, nourishment, or health and wellness benefits.

For purposes of illustration, the interactive aroma dispensing system described herein will be directed to a kiosk, although the disclosure is applicable to any interactive device or environment or system according to the present disclosure. FIG. 1 is a front view of kiosk 100 in accordance with one embodiment of the present disclosure. In the illustrated embodiment, the kiosk 100 includes a housing 110, an aroma blending device 120 (not shown), including a sniffing port 130, and a user interface 140 that can communicate with consumers.

In the illustrated embodiment, the kiosk 100 includes an aroma blending device or scent delivery device 120. In one embodiment, disclosed are systems and devices for on-demand dispensing and delivery of scented substances, e.g., including liquids, vapors or gas. In one embodiment, the aroma blending device 120 may include remote, electrically actuatable scent-release components based on latchable magnetic, piezoelectric, or thermally actuatable switches and mechanisms. In another embodiment, the aroma blending device 120 may use cold diffusion technology, which, for example, generates a scented gas without the use of heating as a primary mechanism to evaporate a scent-carrying liquid. The device 120 may also be structured to include a compartment to hold cartridges containing one or a plurality of scented substances or flavors. In one embodiment, the aroma blending device 120 may be an olfactometer device (an instrument capable of exactly dosing a portion of a gaseous phase which is present due to the vapor pressure of a sample or in the form of a liquid or a solid) for example the Virtual Aroma Synthesizer® device or miniVAS™ device, both developed and owned by Givaudan.

In one embodiment, aroma blending device 120 may include input/output hardware 200, a processor 210 and a memory component 220. The input/output hardware 200 may include and/or be configured to interface with the user interface 140 for receiving, sending, and/or presenting data. The processor 210 may include any processing component operable to receive and execute instructions, such as from the memory component. The memory component 220 may be configured as volatile and/or nonvolatile memory and, as such, may include random access memory (including SRAM, DRAM, and/or other types of RAM), flash memory, secure digital (SD) memory, registers, compact discs (CD), digital versatile discs (DVD), and/or other types of non-transitory computer-readable mediums. Depending on the particular embodiment, these non-transitory computer-readable mediums may reside within the IADS and/or external to the kiosk 100.

Figure 2:
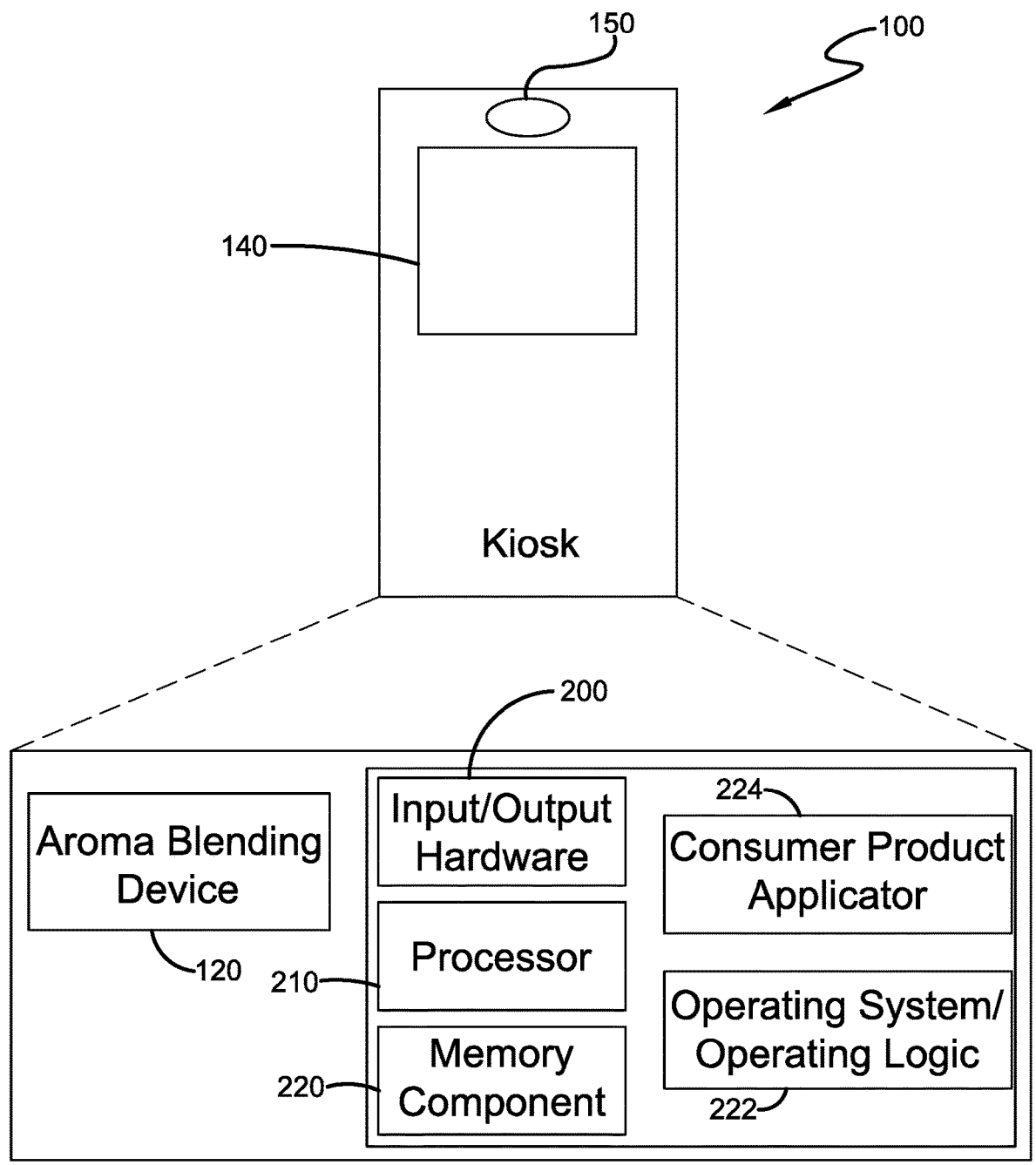
FIG. 2 depicts an interactive aroma dispensing system of FIG. 1 according to embodiments shown and described herein.

It should be understood that the components illustrated in FIG. 2 are merely exemplary and are not intended to limit the scope of this disclosure.

Additionally, the memory component may be configured to store operating logic 222, aroma blending device 120 software applications and consumer product application 224. The operating logic 222 may include an operating system and/or other software for managing components of the kiosk 100. In one embodiment, the blending of the aroma substances is performed using software loaded onto the aroma blending device 120. An example of such software is Aroma Composer™ Software developed by Givaudan Flavors Corporation of Cincinnati, Ohio. The Aroma Composer™ Software controls the ratios and intensities of the ingredient samples or aroma substances delivered to the sniffing port 130 for evaluation by a consumer.

In another embodiment, the automated real-time data analysis of the input information of the consumer may be performed using a software algorithm loaded onto the aroma blending device 120. An example of such software is ATOM™ Software developed by Givaudan Flavors Corporation of Cincinnati, Ohio. The ATOM™ software uses data science and predictive analytics to analyze the data collected from consumers in real-time.

In another embodiment, the memory component 220 may include a consumer product application 224 that operationally interfaces with consumers via visual and/or audible signals, textual instructions, animations, videos, dialogue boxes, selector buttons, icons, prompts and/or other features provided to consumers via the user interface 140. In one example, the consumer product application 224 interfaces with consumers via a plurality of virtual menu options and sub-options that allow consumers to answer questions or input information to the kiosk 100. In one embodiment, the user interface 140 may include at least one display screen, 3D projector and/or a touch screen that can provide information to and receive information from consumers. The user interface 140 may be configured to receive input information from a consumer regarding sensorial characteristics associated with the at least one aroma substance. Many different types of touch screens may be used in accordance with the present disclosure. Some examples of touch screens include resistive, capacitive, surface acoustic wave, infrared, strain gage (i.e., force panel), optical, dispersive signal, acoustic pulse, and coded LCD. Generally, the touch screens should be compatible with a retail environment and be resistant to liquids and common kitchen cleaning chemicals.

In one embodiment, the user interface 140 may be integral or may be a separate component to the kiosk 100. In other embodiments, the user interface 140 may include other input devices that can provide and/or receive consumer information, such as a keyboard, mouse, joystick or other such physical input device, hand gesture recognition means through a camera or by voice activation means through a speaker or smart speaker. Examples of commercially available smart speakers include the "Echo" product available from Amazon.com, Inc. and the "Google Home" product available from Google Inc. Products in this category are arranged to respond to voice commands and to give audio responses to users. Products in this category may offer a voice-implemented intelligent personal assistant software service. In the Amazon Echo device, the personal assistant service has been branded with the name "Alexa". In the Google Home device, the personal assistant service has been branded with the name "Google Assistant". Both of these software-based assistant services are in widespread use.

Input may also be made remotely via an intranet or internet connection, e.g. from a remote computer or smart phone. It is also possible to combine several of these input methods, thereby allowing several users to access the system simultaneously and/or consecutively.

In the illustrated embodiment, the kiosk 100 may further include a support arm 102 for mounting the user interface 140 above or over the kiosk 100. The kiosk 100 may also include one or more detectors 150 for detecting events using an electrically coupled control unit. The detectors 150 can be a variety of one or more devices for receiving an event in direct proximity with the detectors. The detector(s) 150 is shown to be visible, but can otherwise concealed, disguised, or minimized. The detectors 150 can take many forms, for example including cameras, infrared detectors, and accelerometers. The detectors 150 can also take the form of charge-coupled devices (CCD), near-field communication chips (NFC), active pixel sensors (APS), CMOS sensors, and has emerged as an alternative to Charge-coupled device (CCD) sensors, chemical detectors, reverse-biased LEDs, optical detectors, bolometers, pyroelectric detectors, golay cells, thermocouples, thermistors, light dependent resistors (LDR), photovoltaic cells, solar cells, photodiodes, photomultiplier tubes, phototubes, phototransistors, and/or quantum dot photoconductors. The detectors can also be wireless devices configured for one or more wireless technology standards, such as SMS, Bluetooth, 802.11000, or ANT+.

In some embodiments, the detectors 150 can be utilized for detecting various events such as user proximity to the detector, and thereby enter or alter one or more operational modes. Such events can include light intensity detection for ambient light detection, where the touch screen is made dimmer or brighter based on changes in the detected light intensity. In another example, the detectors could detect the presence of a passerby, i.e., someone not in direct proximity to the kiosk 100 and as a result display a commercial, video, or some other attraction on the touch screen to call attention to the kiosk 100 and its availability for use.

In some embodiments, the user can be a normal user or an authorized user holding a certain device, such as an RFID chip or wireless device. As a result of detecting the authorized person through physical presence or receiving a wireless signal, the kiosk 100 may grant access to a managerial screen, such as a service menu described below, for accessing and altering operational modes.

In some embodiments, one or more detectors are used for motion sensing. For example, following a period of no motion, the control system transitions into a predetermined sleep and/or energy saver mode (increasing display life). The recovery from this mode is triggered by the next motion event detected. The manner of the recovery can take several forms. For example, the kiosk can revert to the display that was being displayed prior to sleep mode, such as a screen saver routine. Another example is the playing of a commercial or attraction video on the display of the kiosk for the purpose of calling attention to the kiosk 100 and its availability for use, without the user needing to make direct contact. An attraction video for example, can be a brightly animated or flashing video meant to attract the attention of an indirectly proximate user, i.e., a person standing 3-6 meters away from the kiosk without a direct line of sight to the kiosk 100. This has the advantage of calling attention to the kiosk 100 from a distance.

In another example, a promotional RFID or NFC chip can be attached to a consumer product, such as packaging. Detection of the promotional RFID of NFC chip can result in the kiosk 100 switching display to a promotional message. The kiosk 100 may also include a scanner that can be configured to read bar codes for various consumer products located in the store. For example, the kiosk 100 may include a quick response (QR) scanner that can read a QR code (consists of black modules arranged in a square pattern on white background) imprinted on a product or product packaging. In other embodiments, a two-dimensional barcode can include rectangles, dots, hexagons, and other geometric patterns. Non-limiting examples of two-dimensional barcodes can include CyberCodes, Data Matrices, Datastrip Codes, High Capacity Color Barcodes (HCCB), Dot Codes, EZcodes, mobile multi-colored composites (MMCC), PDF417, ShotCodes, MaxiCodes, SPARQCodes, Snap Tags, and combinations thereof.

In another embodiment, the kiosk 100 may be used to tell the story behind a product. For example, a consumer may scan a vanilla flavored yogurt barcode and the kiosk may show a video that tells the consumer the story behind the creation of the scanned product, i.e. the vanilla flavor comes from vanilla beans grown and harvested in Madagascar, the milk comes from a Wisconsin dairy farm, and while the video is playing consumers could smell aroma of the product.

In another embodiment, the kiosk 100 may also include a receipt or coupon dispenser that can be coupled to a printer within the housing 110. As discussed above, the kiosk 100 can be configured to dispense coupons (for example, $1 off coupons) to a consumer via the dispenser for a product that the consumer indicated that they liked based on the aroma substance that they sampled. In another embodiment, the kiosk 100 may be configured to send the consumer a virtual coupon or discount code via email, text message or an application on a user computing device.

In one embodiment, the kiosk 100 may also communicate with a user computing device. As used herein, the term user computing device refers to any portable device capable of running one or more software applications and also can be connected to the Internet or one or more computer networks. User computing devices include, but are not limited to, smartphones (for example, iPhone or Android), tablets, netbooks, GPS devices, e-readers, iPads, and mobile game consoles (for example, Nintendo DS, Sony PSP). A user computing device may be configured to communicate with the kiosk 100 via a network. In some embodiments, the kiosk 100 may send stored data to the user computing device for later access by a user. As an example, the kiosk 100 may identify the user and receive an indication that the user wishes to be sent information regarding consumer products. Accordingly, the kiosk 100 may send the product information to the user computing device. It should be understood that while the interactive aroma dispensing system is depicted as a kiosk, this is merely an example.

In another embodiment, the kiosk 100 may include comprehensive social media capabilities. For example, the user interface 140 may include a series of display pages suitable for sharing the user's experience at the kiosk 100 with one or more people via a social media website, such as Facebook, Twitter, Instagram, Snapchat, Pinterest, LinkedIn, Google+, YouTube etc in accordance with one aspect of the present disclosure. In one embodiment, a display page on the user interface 140 may provide a consumer with a "log-in" button enabling the user to log-in to a social media account directly from the kiosk 100. The display pages would allow the user to elect to post the results of their interaction with the kiosk 100 to their "profile" or other portion of a social media website. Various embodiments of the display pages referenced above may provide a personalized automated experience through integration with social networks, allowing the consumer to share their individual experiences at the kiosk 100. Integration of the user log-in with preferred social media websites would enable the kiosk 100 operators or sponsors (e.g. a grocery store or consumer product company) to integrate specific information about their products with information provided on the social media site when the consumer logs-in at the kiosk 100. If the consumer logs-in with their social media credentials, a "friends" list can be retrieved and information regarding the friends' interactions with the kiosk 100, for example, favorite aroma of tortilla chips or flavored water, can be displayed for comparison. Further, in another embodiment, a consumer may interact with kiosk 100 and social media websites via a user computing device.

In operation, the user interface 140 may be a touch screen in which a consumer touches the touch screen which causes a command signal to be sent to a processor 210. In response to the received command signal, the processor may send a new graphical configuration to the touch screen. The new graphical configuration may be a screen with a plurality of selectable options. The options may be configured as discernable buttons that indicate different kinds of consumer products, for example, beverages. It should be understood, that a "button" with respect to the touch screen is intended to mean a zone on the touch screen which is predetermined to respond to a touch by a user. For example, the entirety of the touch screen may be considered a button when the sleep mode is displayed, while only select portions of the welcome screen or other screens are considered buttons.

Figure 3:
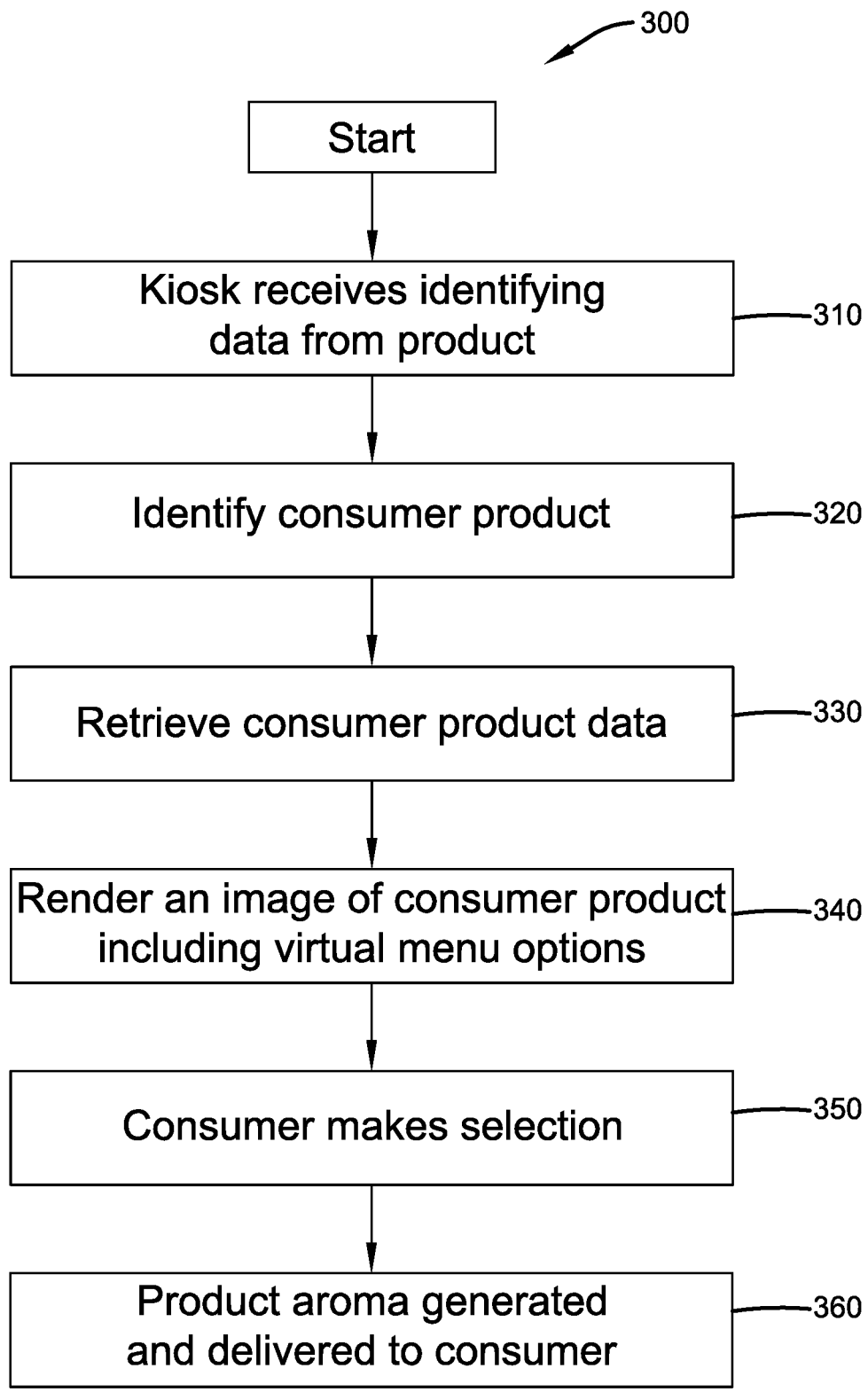
FIG. 3 depicts a flowchart for sampling an aroma associated with an in-store consumer product, according to embodiments shown and described herein.

According to the present disclosure, methods are described for sampling an aroma(s) associated with an in-store consumer product(s). Referring now to FIG. 3, method 300 for sampling an aroma associated with an in-store consumer product includes the steps of: step 310, the kiosk 100 can receive identifying data from a consumer product, such as from markers, from scanning a bar code or QR code, from an image capture device or from a wireless communication between kiosk 100 and a consumer product. At step 320, the kiosk 100 can identify the consumer product. At step 330, the kiosk 100 can retrieve product data from a local and/or remote location. At step 340, the kiosk 100 can render an image of the product in order to provide an interactive interface with a plurality of menu options, including an option to sample the aroma associated with the chosen consumer product. At step 350, the consumer selects his or her choice, for example, by touching the user interface 140. At step 360, the aroma blending device 120 generates an at least one aroma substance for the selected consumer product and delivers the generated aroma substance to the nasal cavities of consumer.

In one embodiment, the kiosk 100 may also provide the consumer with other menu options including the ability to sample the aroma of other products in the same line-up or array. For example, if the consumer product selected is an orange flavored beverage, once the consumer has smelled the orange flavor according to method 300, the kiosk 100 may provide the consumer with the option of also smelling a cherry or grape version of the same beverage in order to determine which flavor the consumer prefers. In another example, if the consumer product selected is nacho cheese flavored tortilla chips, once the consumer has smelled the nacho cheese flavor according to method 300, the kiosk 100 may provide the consumer with the option of also smelling other flavors in the same line-up or array (e.g., salsa verde, spicy nacho, cool ranch, sweet chili or buffalo) in order to determine which flavor or flavors the consumer prefers. The kiosk 100 may also provide the consumer the ability to rank the products in order of liking or preference and to share this information via social media as discussed above.

In another embodiment, the kiosk 100 may also recommend other beverages or products with an aroma profile that best matches the one preferred by the consumer. In one embodiment, method 300 may be carried out in a grocery store, department store, big-box store, restaurants or other retail establishments with the aid of a kiosk 100.

Figure 4:
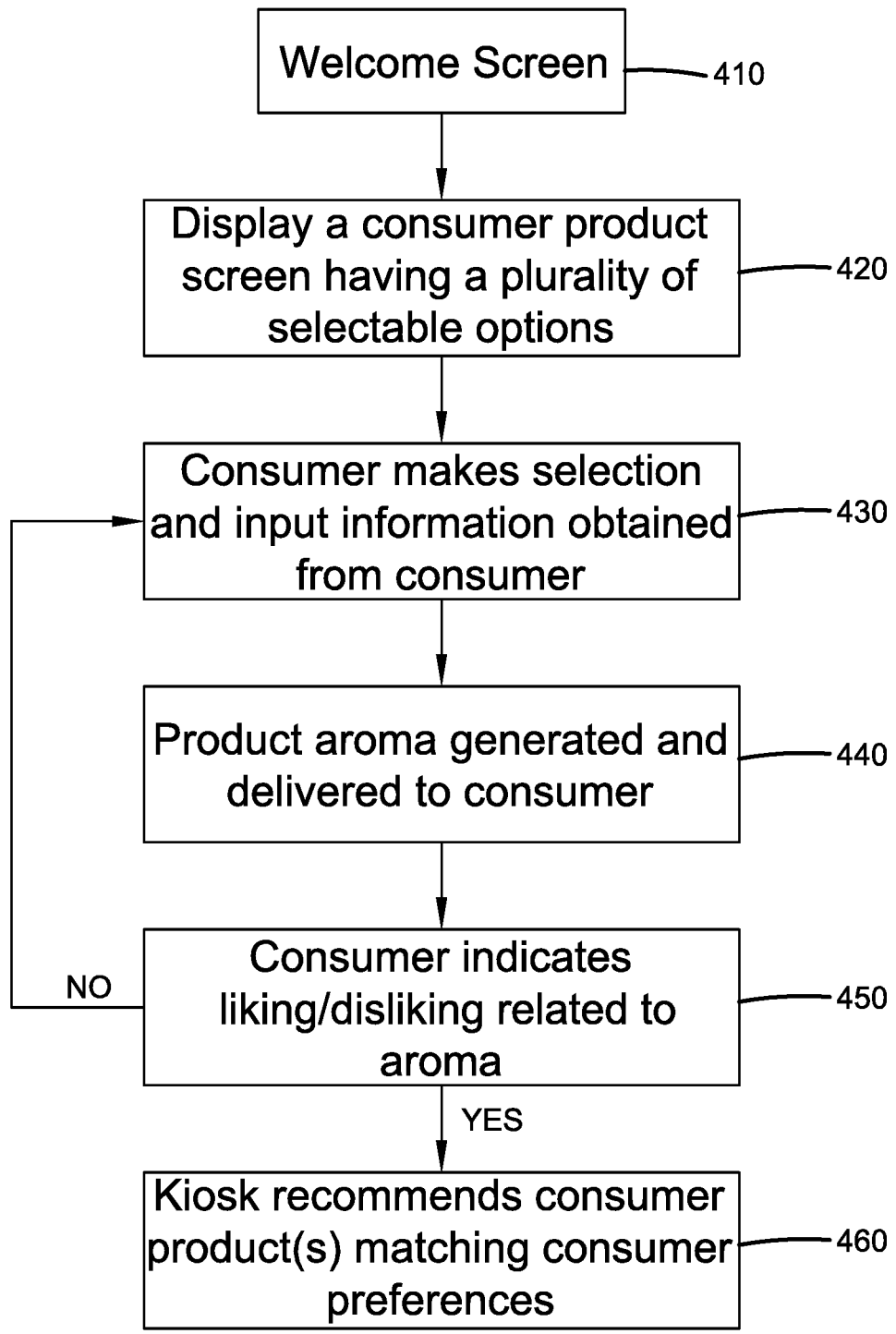
FIG. 4 depicts a flowchart for recommending one or more in-store consumer products matching to a consumer's aroma preferences, according to embodiments shown and described herein.
Figure 4A:
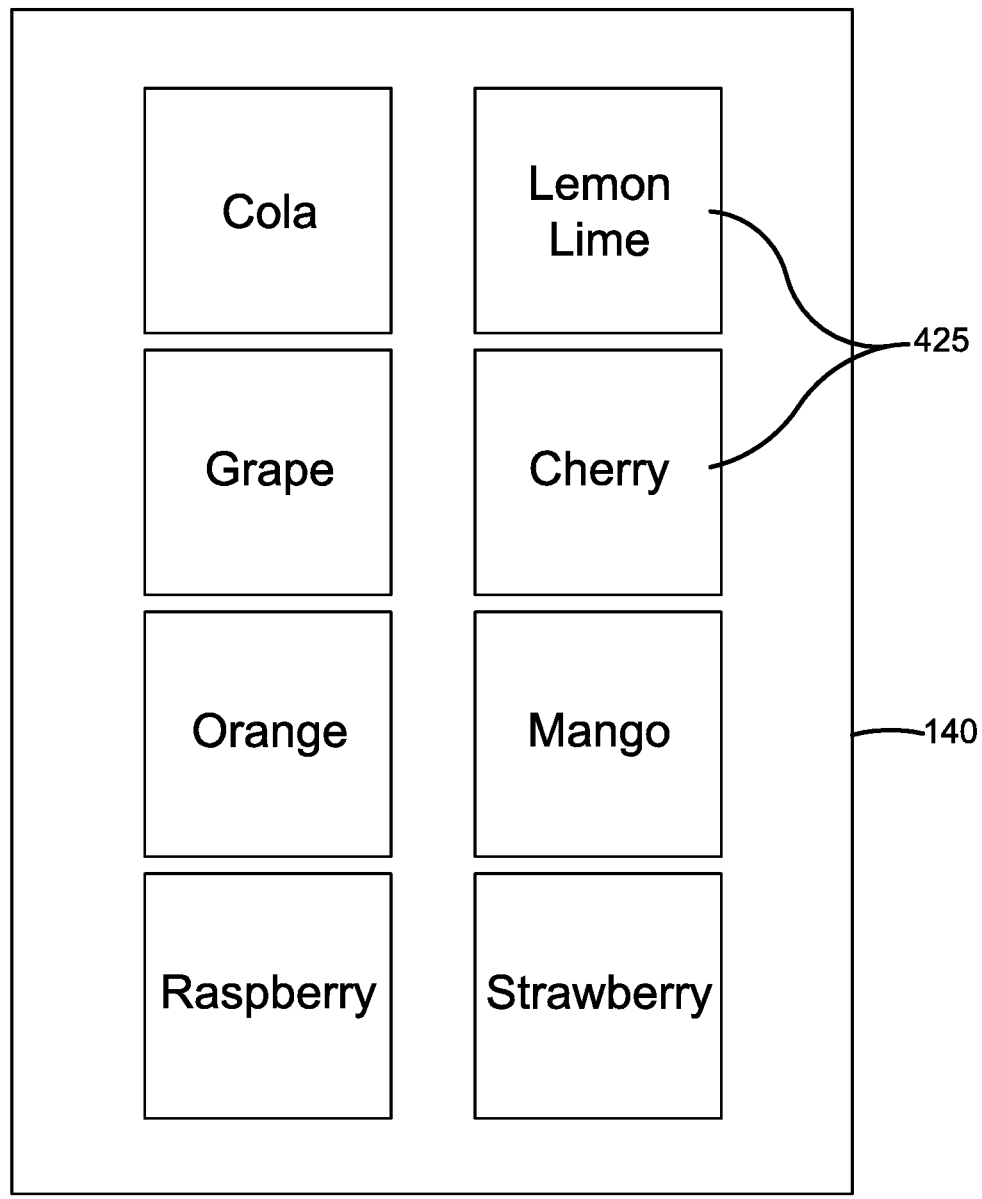
FIG. 4A depicts a screen shot which may be used and is an example of block 420 within FIG. 4.

Referring now to FIG. 4, method 400 for recommending one or more in-store consumer products matching to a consumer's aroma preferences includes the steps of: step 410 includes a welcome screen which identifies the kiosk 100 and any associated food and/or beverage products that may be using the kiosk 100 for marketing. Referring to FIG. 4A, step 420, displays a screen having a plurality of selectable options related to in-store consumer products and associated aromas. In one embodiment, the screen may have a plurality of selectable options related to flavored beverages. The options may be configured as discernable buttons 425 that indicate different flavors of beverages. In the example shown in FIG. 4A, eight discernable buttons 425 are shown, although more or less may be used depending on the desired amount of flavors.

At step 430, a consumer may make a selection from the options and input information is collected from consumer regarding at least one in-store consumer product. In one embodiment, input information may be collected from a consumer by a self-assessment, i.e., questioning means, that is, by the consumer's answering questions, which are asked of him or her, electronically, such as via the display on the kiosk 100. A consumer may submit answers to the questions by typing on a keyboard, touching a responsive screen, speaking an answer, or the like. With regard to step 430, the precise manner and wording chosen to collect input information from the consumer may vary depending on local custom, the comfort level of consumers in discussing food and beverage characteristics, and the meaning associated with terms which may be used in different parts of the world to collect information desired. It is to be further understood that the methods of the present disclosure are not to be limited to any one type of question asking methodology or philosophy.

Figure 5:
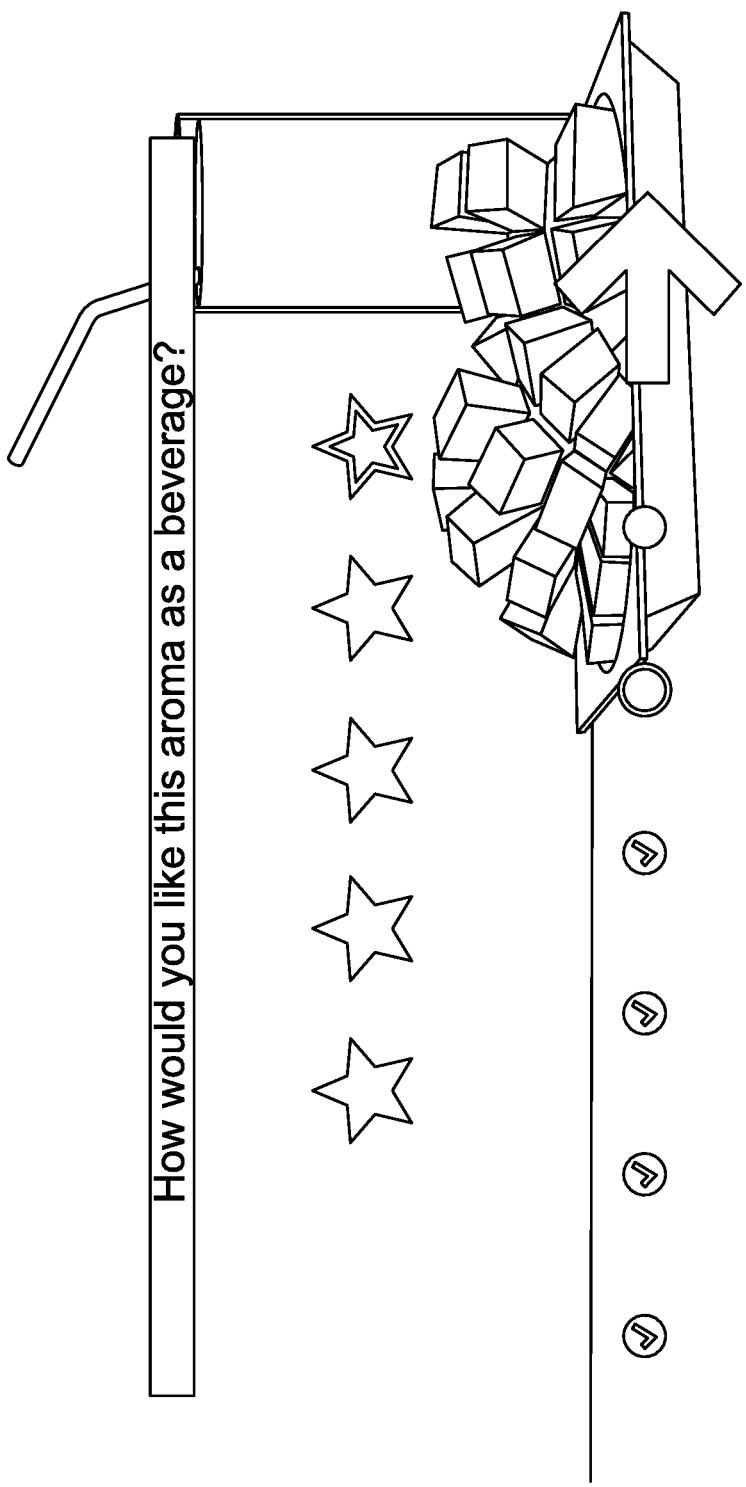
FIG. 5 depicts a screen shot which may be used and is an example of block 450 within FIG. 4.

At step 440, the aroma blending device 120 generates at least one aroma substance for the selected consumer product and delivers the generated aroma substance to the nasal cavities of consumer. At step 450, user preference(s) are received related to the generated aroma substance. In one embodiment, if the consumer in step 450 indicates that the selected aroma is not liked or preferred, the process may return to step 430 for another selection. In one example, during step 450, a rating scale may be displayed on the touch screen in order to capture the preference of the consumer. For example, in FIG. 5, a screen shot of a sample scale is shown that uses a scale from one to five stars for the consumer to indicate liking. At step 460, the kiosk 100 recommends one or more in-store consumer products matching to the consumer's aroma preferences. In another embodiment, the kiosk 100 may include a bar code scanner or QR scanner that could scan the code of various consumer products and predict and inform a consumer of a projected liking or disliking of a product based on the consumer's input at step 450.

In one embodiment, method 400 may be carried out in a grocery store, department store, big-box store or other retail establishment with the aid of a kiosk 100.

In another embodiment, the kiosk 100 may be used as a marketing device. For example, a beverage company may wish to use the kiosk 100 as part of a new to the market product launch, with the goal being that after interaction with the kiosk 100, a consumer will be more likely to purchase the new product. In one embodiment, the kiosk 100 can render an image (virtual or authentic) of the new product in order to provide an interactive interface with a plurality of menu options, including an option to sample the aroma associated with the new product. A consumer may sample the aroma of the new product by touching the user interface 140. Next, an aroma blending device generates an aroma substance for the new product and delivers the generated aroma substance to the nasal cavities of consumer. Use of the kiosk 100 as a marketing device enables consumers to experience the aroma(s) of new product(s) prior to making in-store purchasing decisions.

Figure 6:
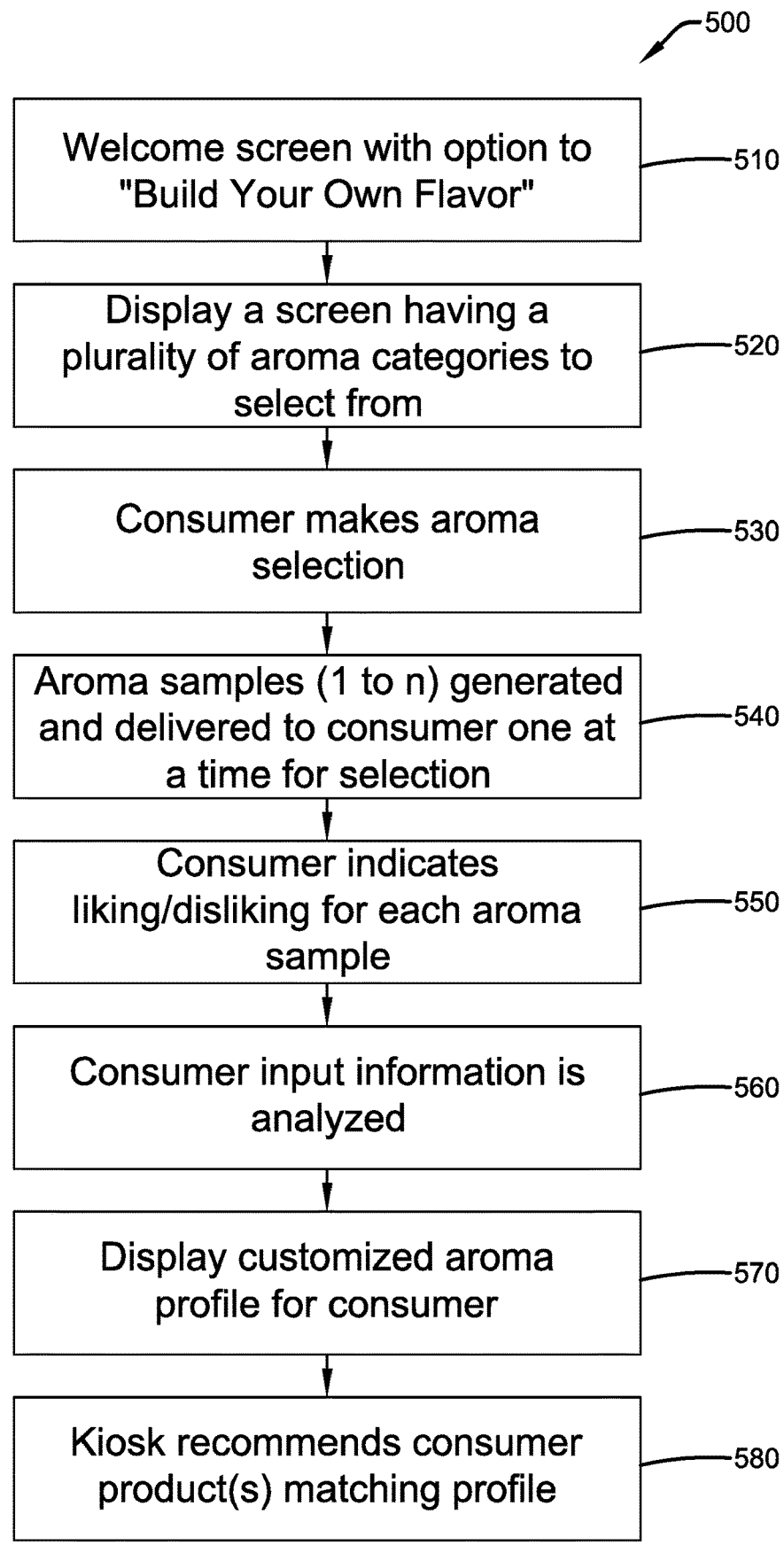
FIG. 6 depicts a flowchart for creating a customized aroma profile for a consumer linked to in-store consumer products, according to embodiments shown and described herein.
Figure 7:
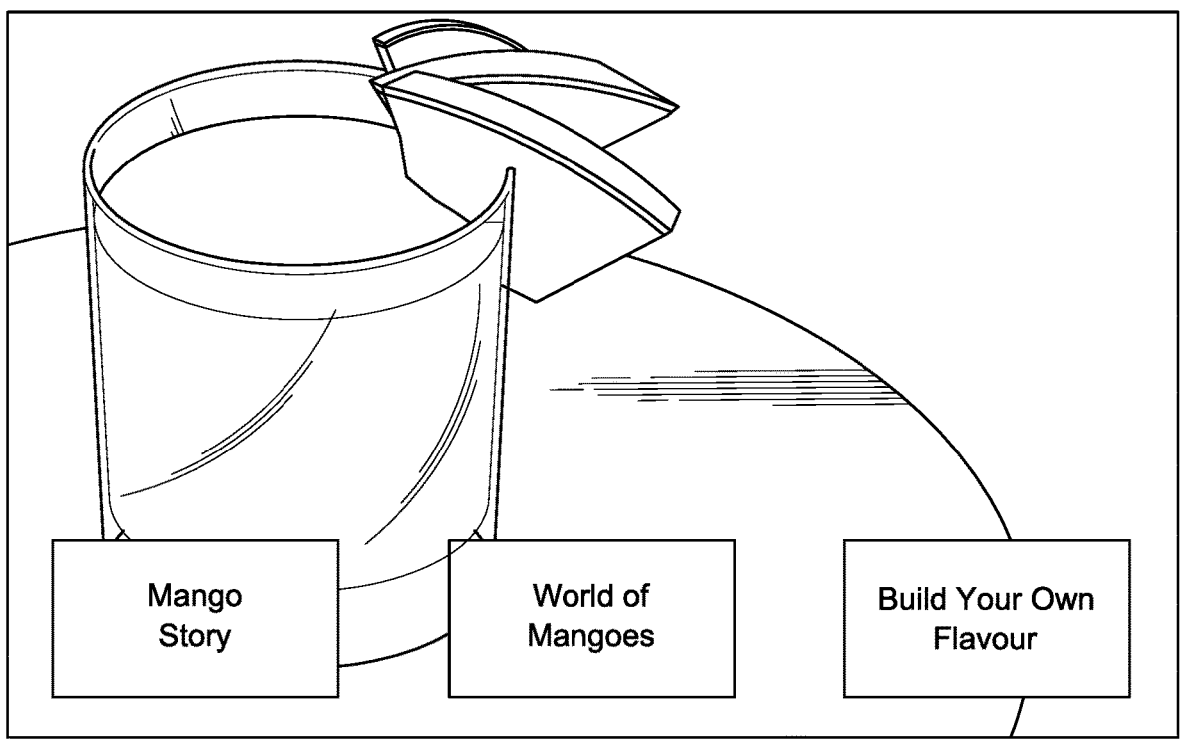
FIG. 7 depicts a screen shot which may be used and is an example of block 510 within FIG. 6.

Referring now to FIG. 6, method 500 for creating a customized aroma profile for a consumer linked to in-store consumer products includes the steps of: step 510 includes a welcome screen (as shown in FIG. 7) which provides a consumer with the option to "Build Your Own Flavor." If the consumer selects this option by selecting the "Build Your Own Flavor" button, step 520 may display a screen having a plurality of aroma categories to choose from. For example, at step 520 the categories may include fruits and berries, vegetables, herbs and spices, dairy, vanilla, mint, meat, poultry, fish and seafood. In one embodiment, a consumer may select the flavor category, for example, fruits and berries. Another screen may then display a plurality of fruits and berries to choose from, for example, mango, strawberry, orange, raspberry, blueberry, watermelon, pineapple etc. At step 530, a consumer may make a selection from the options. Once the consumer drills down and selects the flavor they wish to build, for example, mango, the kiosk 100 will prompt the consumer to begin the process of building a flavor. Other options may include an option to educate consumers about their particular selection through the use of videos or animations, for example a "Story" option or "World" option. At step 540, the kiosk 100 will prepare a plurality of "mango" samples (1-N) for the consumer to smell, for example 5-6 different mango aromas. For each "mango" sample, the aroma blending device 120 generates an aroma substance and delivers it to the nasal cavities of consumer one by one for evaluation.

Figure 8:
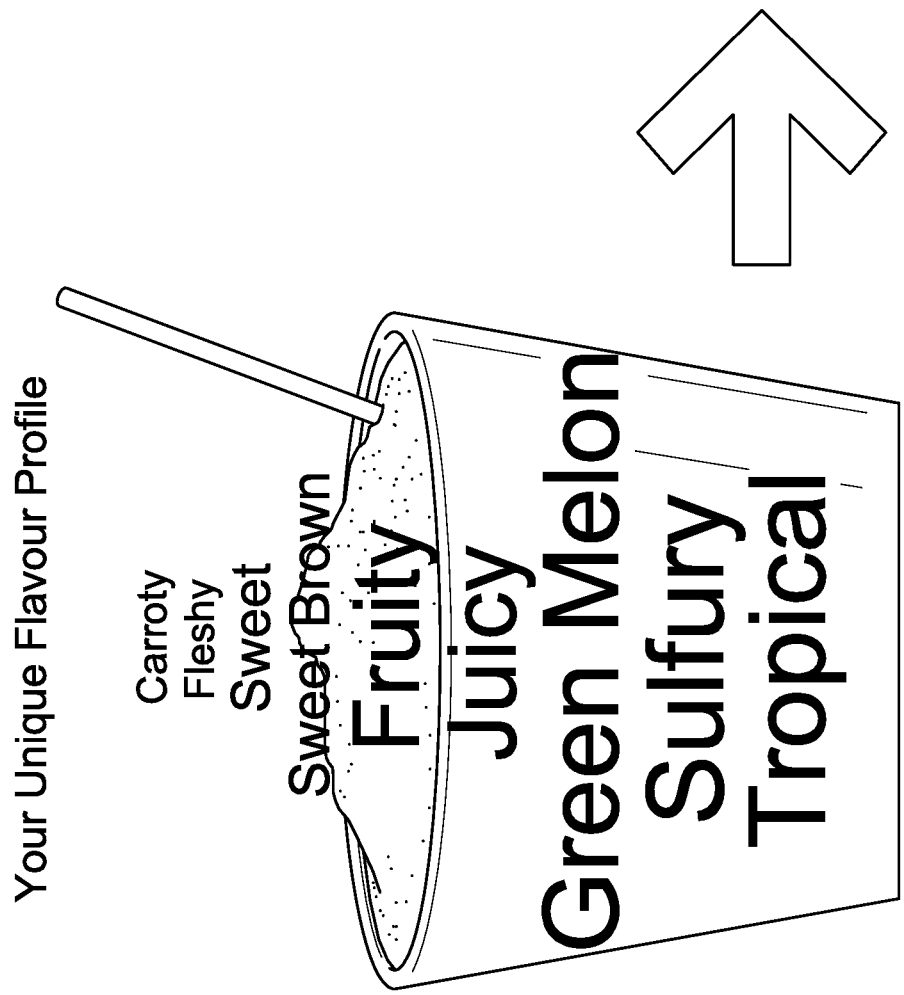
FIG. 8 depicts a screen shot which may be used and is an example of blocks 570 and 580 within FIG. 6.
Figure 8:

At step 550, for each sample, the consumer will indicate whether the aroma is preferred or not preferred. In one example, a rating scale may be displayed on the touch screen in order to capture the preference of the consumer. For example, in FIG. 5, a screen shot of a sample scale is shown that uses a scale from one to five stars for the consumer to indicate liking. The consumer will repeat this process for each sample that is generated by the aroma blending device 120. Still referring to FIG. 6, at step 560, the input information from step 550 is analyzed with the aid of computer hardware and software. For example, the kiosk 100 may use software, for example, ATOM™ software described above. At step 570, the kiosk 100 displays a custom aroma profile for the consumer based on the input information. This custom profile may include a list of sensory characteristics for the selected aroma, both positive and negative, based upon the consumer input in step 540. For example, as shown in FIG. 8, a list of positive and negative mango descriptors may be displayed for the consumer to view, i.e. sulfury, tropical, green melon, carroty, fleshy, fruity, juicy, and sweet. Based upon these sensory characteristics, at step 580, the kiosk 100 recommends one or more in-store consumer products matching to the consumer's aroma profile or preferences for mango. For example, as shown in FIG. 8, the kiosk 100 may recommend the top 3 market products that most closely match the consumer's "liking" profile that resulted from method 500.

In another embodiment, the kiosk 100 may include an option to predict and inform a consumer of a projected liking or disliking of a product based on the consumer's input at step 550. For example, if the consumer is interested in purchasing a mango yogurt or mango beverage, the kiosk 100 could recommend that the consumer would most likely prefer DANNON mango yogurt over CHOBANI mango yogurt or BUBLY mango water over BAI mango water. In another embodiment, the kiosk 100 may also dispense a coupon for the recommended product.

According to another embodiment, the kiosk 100 may be used for consumer understanding or consumer preference testing. For example, a group of consumers could be pre-selected or walk-in to the kiosk 100 in a public place, and each consumer would use the kiosk 100 to sample a number of different aromas or profiles. After each sample the consumer may indicate a liking or disliking of the sample and the consumer's choices may be ranked. This type of consumer insight information is very valuable to companies. Such consumer insight may be used by companies to understand what is now and what is next for flavor or fragrance trends; flavor drivers; examine attitudes toward new flavors or fast-growing ingredients; learn how consumer preferences are changing and learn what flavors or fragrances are trending upwards; uncover impactful insights about a specific brand; measure brand equity, perception and performance against a competitive set; and identify strengths and weaknesses of a brand. In another embodiment, a food or beverage company may use the kiosk 100 for a pilot test before launching a new product.

All of these insights may be gathered by a company thru use of the kiosk 100 and could be used for product development and to answer the questions "What kind of flavors do consumers prefer?" For example, a company may use the kiosk 100 to gather insight with respect to yogurt and some typical information may include: "flavor" drives more than half (54%) of consumers yogurt purchases, with berry tops among both adults (60%) and children (58%); Tropical isn't far behind, with 43% and 47% of adults and parents citing it, respectively; Vanilla has fans among adults (46%) and children (43%), but coffee wins with only 20% of Baby Boomers and 18% of 15-to-17-year-olds; Flavors like "vegetable" and "botanical/floral" appeal to Gen Xers and Boomers alike, and even 22% of 3-to-5-year-olds consume "vegetable" yogurt; Gen Z consumers are the biggest patrons of "spicy" flavors even if at only 6% while those in the Silent Generation don't care for "spicy" yogurt at all; As for yogurt styles and formats, by asking question using the kiosk 100, 28% of adults and 68% of children are happy to drink their yogurt; "Greek" yogurt is the most popular style with adults (55%); children, on the other hand, prefer whole-milk yogurt at a rate of 50%; Only 19% of adults eat packaged yogurt with add-ins or toppings, but 25% of children enjoy products with such inclusions.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An aroma dispensing system, comprising:
   an aroma blending device configured to deliver at least one aroma substance characteristic of an in-store consumer product to the nasal cavities of a consumer, wherein the in-store consumer product is selected from at least one of consumables, cosmetics, personal care products, air freshening sprays, laundry detergents and additives, room fresheners, room deodorants, household cleansers, toilet bowl cleaners, or dish detergents;
   a user interface configured for receiving input information from a consumer and displaying information regarding sensorial characteristics associated with the at least one aroma substance characteristic of the in-store consumer product;
   means selected from an image capture device, a scanner, or a wireless connection between the aroma dispensing system and the in-store consumer product, for receiving identifying data from the in-store consumer product and for identifying the in-store consumer product;
   means for displaying an image of the in-store consumer product along with at least one menu option, including a menu option for selecting one of said in-store consumer product and sampling an aroma associated with a selected in-store consumer product;
   means for retrieving product data for the in-store consumer product; and
   a memory component that stores a computer algorithm, the computer algorithm causing the system to analyze the consumer input information in real-time in order to classify aroma preferences of the consumer, including recommending one or more of said in-store consumer products suitable to the consumer's aroma preferences.

2. The system according to claim 1, wherein the user interface is a touch screen.

3. The system according to claim 1, further comprising a consumer product application.

4. The system according to claim 3, the consumer product application further causing the system to provide, in response to selection of a first menu option, a plurality of menu sub-options.

5. The system according to claim 1, further comprising at least one of the following:
   a camera for capturing an image of a product and sending data associated with the product to the memory component;
   a scanner for capturing a code identifying a product and sending data associated with the product to the memory component; and
   a printing device for printing data regarding the product, wherein the data regarding the first product includes at least one of the following: a coupon, a rebate, product use information, and product feature information.

6. The system according to claim 1, wherein the aroma blending device comprises a sniffing port.

7. The system according to claim 1, wherein the aroma blending device comprises remote, electrically actuatable scent-release components based on latchable magnetic, piezoelectric, or thermally actuatable switches and mechanisms.

8. The system according to claim 1, wherein the aroma blending comprises an olfactometer device.

9. A method for sampling an aroma associated with an in-store consumer product using a kiosk comprising the steps of:

(a) receiving identifying information from said at least one in-store consumer product by means selected from an image capture device, a scanner, or a wireless connection between the kiosk and the in-store consumer product, wherein said at least one in-store consumer product is selected from at least one of consumables, cosmetics, personal care products, air freshening sprays, laundry detergents and additives, room fresheners, room deodorants, household cleansers, toilet bowl cleaners, or dish detergents;

(b) identifying the in-store consumer product using the received identifying information;

(c) retrieving product data for the identified in-store consumer product;

(d) displaying an image of the identified in-store consumer product along with at least one menu option;

(e) selecting the menu option to sample the aroma associated with the identified in-store consumer product;

(f) generating at least one aroma substance associated with the selected in-store consumer product; and (g) delivering the generated aroma substance to the nasal cavities of a consumer.

10. The method according to claim 9, wherein steps (f) and/or (g) are carried out by an aroma blending device.

11. The method according to claim 10, wherein the aroma blending device comprises a sniffing port.

12. The method according to claim 9, wherein a user interface is utilized to carry out steps (d) and (e).

* * * * *